(12) United States Patent
Furukawa et al.

(10) Patent No.: US 6,962,921 B2
(45) Date of Patent: Nov. 8, 2005

(54) DEMENTIA REMEDIES CONTAINING 2-ARYL-8-OXODIHYDROPURINE DERIVATIVES AS THE ACTIVE INGREDIENT

(75) Inventors: Kiyoshi Furukawa, Shiga-gun (JP); Satoshi Kurumiya, Nishinomiya (JP); Takashi Hashimoto, Nishinomiya (JP)

(73) Assignee: Dainippon Pharmaceutical Co., Ltd., Osaka-fu (JP)

( * ) Notice: Subject to any disclaimer, the term of this patent is extended or adjusted under 35 U.S.C. 154(b) by 0 days.

(21) Appl. No.: 10/343,453

(22) PCT Filed: Jul. 24, 2001

(86) PCT No.: PCT/JP01/06363

§ 371 (c)(1), (2), (4) Date: Jan. 31, 2003

(87) PCT Pub. No.: WO02/10167

PCT Pub. Date: Feb. 7, 2002

(65) Prior Publication Data

US 2003/0166667 A1 Sep. 4, 2003

(30) Foreign Application Priority Data

Jul. 31, 2000 (JP) ........................................ 2000-230209

(51) Int. Cl.⁷ ...................... C07D 473/00; A61K 31/52; A61P 25/28; A61P 25/00
(52) U.S. Cl. .................................... 514/263.3; 544/265
(58) Field of Search ...................................... 514/263.3

(56) References Cited

U.S. PATENT DOCUMENTS

| | | | | |
|---|---|---|---|---|
| 5,380,739 A | * | 1/1995 | Clark et al. | 514/381 |
| 5,453,428 A | * | 9/1995 | Kaminski | 514/279 |
| 5,470,868 A | * | 11/1995 | Young | 514/397 |
| 6,372,740 B1 | | 4/2002 | Murata et al. | |

FOREIGN PATENT DOCUMENTS

| | | | | |
|---|---|---|---|---|
| EP | 0 882 727 | | 12/1998 | |
| JP | 2001048882 A | * | 2/2001 | ......... C07D/473/00 |
| WO | 99/28320 | | 6/1999 | |

OTHER PUBLICATIONS

"A Depression Symptoms Checklist", <http://www.pueblo.gsa.gov/cic_text/health/over–65/symptoms.htm> downloaded from the Internet Nov. 23, 2004.*
"Epilepsy and memory" <http://www.epilepsy.com/epilepsy/memory.html> downloaded from the Internet Nov. 23, 2004.*
Munoz, CMAJ 2000;162:65–72.*
Palmer TRENDS in Pharmacological Sciences 23(9) 426–433 Sep. 2002.*
E. Romeo et al., "Mitochondrial Diazepam–Binding Inhibitor Receptor Complex Agonists Antagonize Dizocilpine Amnesia: Putative Role for Allopregnanolone", The Journal of Pharmacology and Experimental Therapeutics, vol. 270, No. 1, pp. 89 to 96, 1994.

Patent Abstracts of Japan, Abstract of JP 2001–048882, Published Feb. 20, 2001.
James F. Flood et al., "Dehydroepiandrosterone Sulfate Improves Memory in Aging Mice", Brain Research, vol. 448, pp. 178–181, 1988.
James F. Flood et al., "Memory–enhancing Effects in Male Mice of Pregnenolone and Steroids Metrobolically Derived from it", Proc. Natl. Acad. Sci., vol. 89, pp. 1567–1571, Mar. 1992.
E. Romeo et al., "2–Aryl–3–Indoleacetamides (FGIN–1): A New Class of Potent and Specific Ligands for the Mitochondrial DBI Receptor (MDR)", The Journal of Pharmacology and Experimental Therapeutics, vol. 262, No. 3, pp. 971–978, 1992.
Dennis J. Selkoe, "Biochemistry of Altered Brain Proteins in Alzheimer's Disease", Ann. Rev. Neurosci, vol. 12, pp. 463–490, 1989.
C.G. Gottfries, "Alzheimer's Disease and Senile Dementia; Biochemical Characteristics and Aspects of Treatment", Psychopharmacology, vol. 86, pp. 245–252, 1985.
Joseph T. Coyle et al., "Alzheimer's Disease: A Disorder of Cortical Cholinergic Innervation", Science, vol. 219, pp. 1184–1190, 1983.
Spravochnik–poutivoditel praktikouyuschego vracha, 2000 diseases from A to Z, Moscow, GEORAR Meditgsina, pp. 288–289 and translation.

* cited by examiner

Primary Examiner—Mark L. Berch
(74) Attorney, Agent, or Firm—Wenderoth, Lind & Ponack, L.L.P.

(57) ABSTRACT

Medicines for treatment or prevention of dementia comprising 2-aryl-8-oxodihydropurine derivatives of the formula (I):

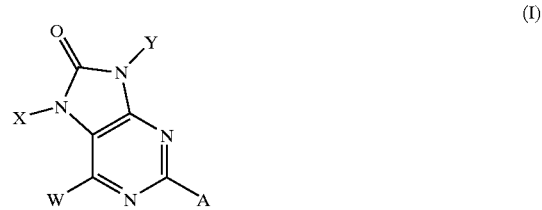

wherein W is H, $C_{1-6}$ alkyl, halogen, $C_{1-6}$ alkoxy, or the like; X is H, $C_{1-6}$ alkyl, a group of the formula (Q): —CH($R^3$)CON($R^1$) ($R^2$) (wherein $R^1$ is a $C_{1-6}$ alkyl or the like; $R^2$ is phenyl-substituted $C_{1-4}$ alkyl or the like; and $R^3$ is H or the like); Y is H, $C_{1-6}$ alkyl, a group of the above formula (Q), or the like; and A is substituted phenyl or the like, with the proviso that one of X and Y is a group of the formula (Q) and the other is a group selected from those defined for X or Y except the groups (Q), or pharmaceutically acceptable acid addition salts thereof. The above compounds exhibit an extremely potent ameliorating effect on learning disorder and/or dymnesia and thus are useful in the treatment or prevention of Alzheimer-type dementia, cerebrovascular dementia, senile dementia, etc.

4 Claims, No Drawings

DEMENTIA REMEDIES CONTAINING 2-ARYL-8-OXODIHYDROPURINE DERIVATIVES AS THE ACTIVE INGREDIENT

TECHNICAL FIELD

The present invention relates to a medicine for treatment of dementia comprising a 2-aryl-8-oxodihydropurine derivative, in more detail, a 2-aryl-8-oxodihydropurine derivative which has an acetamide moiety at the 7- or 9-position of the purine ring.

BACKGROUND ART

With the advance of aging of society, the increase of patients suffering from dementia has been causing a social problem, and about 90% thereof is occupied with Alzheimer-type dementia and cerebrovascular dementia. With respect to the symptom of dementia, short- and long-term dysmnesia is a fundamental and common core symptom, therefore it is considered that the dementia is composed of dysmnesia, disorientation due to dysmnesia and higher brain dysfunction associated therewith. In the patients suffering from dementia, the functions of various neurotransmitter systems are remarkably decreased mainly in the cerebral cortex and the limbic system, additionally the function of cerebral energy metabolism is also decreased. Especially in the patients with Alzheimer-type dementia, the hypofunctions of neurotransmission are found in cholinergic, glutamatergic, neuropeptidergic and monoaminergic system, and it is suggested that the main cause of Alzheimer-type dementia is dysfunction of such neurotransmitter systems [Coyle, J. T. et al., Science, 219, 1184–1190 (1983); Gottfries, C. G. et al., Psychopharmacology, 86, 245–252 (1985)]. Besides, from the viewpoint of the neurotoxicity induced by β-amyloid peptide, it is guessed that the loss of hippocampal neurons through the accumulation of β-amyloid peptide in senile plaque on the surface of the cell is involved in the mechanism of disease onset, and is also one of the main causes of Alzheimer-type dementia [Selkoe D. J., Annu. Rev. Neurosci., 12, 463–490 (1989)].

On the basis of the finding that the remarkable neuronal dysfunction associated with cholinergic system is a cause of dysmnesia in dementia as suggested above, the medicines for improving the symptoms of dementia by means of the activation of cholinergic system have been developed. Further, on giving attention to the decrease of glutamatergic neurons and N-methyl-D-aspartic acid (hereinafter, abbreviated to "NMDA") receptors, which is one of receptors of glutamic acid, a medicine to activate the NMDA receptor function has been also developed.

Recently, there are also some attempts to develop agonists for the peripheral-type benzodiazepine (hereinafter, optionally abbreviated to "BZ$\omega_3$") receptors as the therapeutic agent for improvement in the symptoms of dementia. For example, it has been reported that N,N-di-n-hexyl-2-(4-fluorophenyl)indol-3-acetamide (hereinafter, abbreviated to "FGIN-1-27") which is an agonist for BZ$\omega_3$ receptors, and some kinds of neurosteroids (for example, pregnenolone sulfate, allopregnanolone) have weak ameliorating effects in the animal models of learning impairment (active avoidance test, the radial-arm maze test, and water maze test) [Flood, J. F. et al., Brain Res., 448, 178–181 (1988); Flood, J. F. et al., Proc. Natl. Acad. Sci. U.S.A., 89, 1567–1571 (1992); Romeo, E. et al., J. Pharmacol. Exp. Ther., 270, 89–96 (1994)].

Until now, a lot of studies on the function of BZ$\omega_3$ receptors have been reported, and hence it has been shown that in the brain, BZ$\omega_3$ receptors often exist on the outer membrane of mitochondria in the glial cells and are involved in the uptake of cholesterol into the inner membrane of mitochondria, and then affect the biosynthesis of neurosteroids such as pregnenolone and consequently allopregnanolone and allotetrahydrodeoxycorticosterone. That is to say, it is considered that the stimulation onto the BZ$\omega_3$ receptor promotes the biosynthesis of neurosteroids in the brain, and these neurosteroids bind to the neurosteroid-recognition site (different site from the benzodiazepine receptor) in the complex of γ-aminobutyric acid A (hereinafter optionally abbreviated to "GABA-A") receptor—benzodiazepine receptor—Cl-ionchannel and affect the Cl-channel opening process [Romeo, E. et al., J. Pharmacol. Exp. Ther., 262, 971–978 (1992)].

Since BZ$\omega_3$ receptor agonists modulate the function of GABA-A receptors via the biosynthesis of neurosteroids, it is suggested that the BZ$\omega_3$ receptor agonists could be possibly used as anxiolytics, antidepressants, hypnotics, antiepileptics, etc. For example, WO 99/28320 discloses that 2-aryl-8-oxodihydropurine derivatives of the formula (I), are selective and high-affinity BZ$\omega_3$ receptor agonists and are useful as medicines for treatment of, for example, anxiety-related disorders and depression.

In addition to the above, there are some other reports indicating that the BZ$\omega_3$ receptor agonists exhibit anxiolytic actions, but it is scarcely reported that said agonists exhibit an ameliorating effect on learning impairments, except for the above report as to FGIN-1-27.

DISCLOSURE OF INVENTION

The BZ$\omega_3$ receptor agonists have a different mechanism of action from those of the known anti-dementia medicines, and then it seems that it is possible to provide a useful anti-dementia medicine with a different property from the current medicine for dementia, if a compound with a potent ameliorating effect on dementia could be found among them.

The present inventors have extensively studied to find out the compound having a potent ameliorating effect on dementia among the known BZ$\omega_3$ receptor agonists, and have found that 2-aryl-8-oxodihydropurine derivatives of the formula (I) and pharmaceutically acceptable acid addition salts thereof exhibit unexpectedly potent ameliorating effects on learning and/or memory impairments in animals, said impairments being induced by the systemic administration of MK-801 [dizocilpine maleate; (+)-5-methyl-10,11-dihydro-5H-dibenzo[a,d]cycloheptane-5,10-imine maleate] which is a noncompetitive NMDA receptor antagonist and (−)-scopolamine hydrobromide (hereinafter abbreviated to "scopolamine") which is a competitive acetylcholine receptor antagonist. Based upon the new findings, the present invention has been completed.

An object of the present invention is to provide a medicine for the treatment of dementia comprising a 2-aryl-8-oxodihydropurine derivative which exhibits an extremely potent ameliorating effect on learning and/or memory impairments induced by hypofunction of glutamatergic system or cholinergic system and is useful for the treatment of dementia (e.g. cognitive impairment), such as Alzheimer-type dementia, cerebrovascular dementia and senile dementia. This and other objects and advantages of the present invention will be apparent to a person skilled in the art, from the following description.

The present invention provides a medicine for the treatment or prevention of dementia comprising a 2-aryl-8-oxodihydropurine derivative of the formula (I):

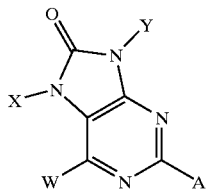

wherein:

W is a hydrogen atom; a $C_{1-6}$ alkyl group; a halogen atom; a $C_{1-6}$ alkoxy group; an amino group; a mono- or di($C_{1-4}$ alkyl)amino group; or a phenyl group which may optionally have 1 or 2 substituents selected from a halogen, a $C_{1-6}$ alkyl, a $C_{1-6}$ alkoxy, trifluoromethyl, hydroxy, amino, a mono- or di($C_{1-4}$ alkyl)amino, cyano and nitro;

X is a hydrogen atom; a $C_{1-6}$ alkyl group; a $C_{3-8}$ cycloalkyl-$C_{1-4}$ alkyl group; a $C_{1-4}$ alkyl group substituted by a phenyl group which may optionally have 1 or 2 substituents selected from a halogen, a $C_{1-6}$ alkyl, a $C_{1-6}$ alkoxy, trifluoromethyl, hydroxy, amino, a mono- or di($C_{1-4}$ alkyl)amino, cyano and nitro; a $C_{3-6}$ alkenyl group; a carbamoyl group; a di($C_{1-4}$ alkyl)carbamoyl group; or a group of the formula [Q]:

—CH($R^3$)CON($R^1$)($R^2$)    [Q]

wherein $R^1$ is a $C_{1-6}$ alkyl group; a $C_{3-6}$ alkenyl group; a $C_{3-8}$ cycloalkyl group; a $C_{3-8}$ cycloalkyl-$C_{1-4}$ alkyl group; or a hydroxy-$C_{1-4}$ alkyl group;

$R^2$ is a $C_{1-6}$ alkyl group; a $C_{3-8}$ cycloalkyl group; a phenyl group which may optionally have 1 or 2 substituents selected from a halogen, a $C_{1-6}$ alkyl, a $C_{1-6}$ alkoxy, trifluoromethyl, hydroxy, amino, a mono- or di($C_{1-4}$ alkyl)amino, cyano and nitro; a $C_{1-4}$ alkyl group substituted by a phenyl group which may optionally have 1 or 2 substituents selected from a halogen, a $C_{1-6}$ alkyl, a $C_{1-6}$ alkoxy, trifluoromethyl, hydroxy, amino, a mono- or di($C_{1-4}$ alkyl)amino, cyano and nitro; or a monocyclic 5- or 6-membered heteroaryl group or a bicyclic heteroaryl group composed of 5- or 6-membered heteroaryls, which have at least one heteroatom selected from a nitrogen atom, an oxygen atom or a sulfur atom, and is optionally substituted by a $C_{1-3}$ alkyl or trifluoromethyl; or $R^1$ and $R^2$ may optionally be taken together with the adjacent nitrogen to form a piperidine ring, a pyrrolidine ring, a morpholine ring or a piperazine ring, which may optionally be substituted by 1 or 2 $C_{1-6}$ alkyls respectively;

$R^3$ is a hydrogen atom, a $C_{1-6}$ alkyl group or a hydroxy-$C_{1-4}$ alkyl group;

Y is a hydrogen atom; a $C_{1-6}$ alkyl group; a $C_{3-8}$ cycloalkyl group; a $C_{3-8}$ cycloalkyl-$C_{1-4}$ alkyl group; a $C_{3-6}$ alkenyl group; a $C_{1-4}$ alkyl group substituted by a phenyl group which may optionally have 1 or 2 substituents selected from a halogen, a $C_{1-6}$ alkyl, a $C_{1-6}$ alkoxy, trifluoromethyl, hydroxy, amino, a mono- or di($C_{1-4}$ alkyl) amino, cyano and nitro; or a group of the formula [Q]:

—CH($R^3$)CON($R^1$)($R^2$)    [Q]

wherein $R^1$, $R^2$ and $R^3$ are as defined above;

A is a phenyl group which may optionally have 1 or 2 substituents selected from a halogen, a $C_{1-6}$ alkyl, a $C_{1-6}$ alkoxy, trifluoromethyl, hydroxy, amino, a mono- or di($C_{1-4}$ alkyl)amino, cyano and nitro; or a monocyclic 5- or 6-membered heteroaryl group or a bicyclic heteroaryl group composed of 5- or 6-membered heteroaryls which have at least one heteroatom selected from a nitrogen atom, an oxygen atom or a sulfur atom, and is optionally substituted by a $C_{1-3}$ alkyl or trifluoromethyl;

with the proviso that either X or Y of the above formula (I) is a group of the above formula [Q], and when X is a group of the formula [Q], then Y is a hydrogen atom; a $C_{1-6}$ alkyl group; a $C_{3-8}$ cycloalkyl group; a $C_{3-8}$ cycloalkyl-$C_{1-4}$ alkyl group; a $C_{3-6}$ alkenyl group; or a $C_{1-4}$ alkyl group substituted by a phenyl group which may optionally have 1 or 2 substituents selected from a halogen, a $C_{1-6}$ alkyl, a $C_{1-6}$ alkoxy, trifluoromethyl, hydroxy, amino, a mono- or di($C_{1-4}$ alkyl)amino, cyano and nitro, and when Y is a group of the formula [Q], then X is a hydrogen atom; a $C_{1-6}$ alkyl group; a $C_{3-8}$ cycloalkyl-$C_{1-4}$ alkyl group; a $C_{1-4}$ alkyl group substituted by a phenyl group which may optionally have 1 or 2 substituents selected from a halogen, a $C_{1-6}$ alkyl, a $C_{1-6}$ alkoxy, trifluoromethyl, hydroxy, amino, a mono- or di($C_{1-4}$ alkyl)amino, cyano and nitro; a $C_{3-6}$ alkenyl group; a carbamoyl group; or a di($C_{1-4}$ alkyl)carbamoyl group; or a pharmaceutically acceptable acid addition salt thereof (hereinafter abbreviated to "compound of the present invention").

More specifically, the present invention provides a medicine for treatment or prevention of Alzheimer-type dementia, cerebrovascular dementia, and/or senile dementia comprising as an active ingredient the compound of the above formula (I).

Further, as an embodiment of improving dysfunction, a medicine for improvement in learning and/or memory impairments in mammals (including human beings) is provided.

A pharmaceutically acceptable acid addition salt of the compound of the formula (I) denotes a pharmaceutically acceptable acid addition salt of the compound of the formula (I) which has a sufficient basicity so as to form a acid addition salt, for example, inorganic acid salts such as hydrochloride, hydrobromide, hydroiodide, sulfate, or phosphate, and organic acid salts such as maleate, fumarate, oxalate, citrate, tartrate, lactate, benzoate, or methanesulfonate.

The compounds of the present invention and acid addition salts thereof of the formula (I) may optionally exist in the form of hydrate form and/or solvate, and these hydrates and solvates thereof are included in the present invention.

The compounds of the formula (I) may optionally have at least one asymmetric carbon and also optionally have geometrical isomers. Thus, the compounds of the formula (I) may occasionally exist as two or more stereoisomers, and the compounds of the present invention may include said stereoisomers, a mixture thereof and racemate.

2-Aryl-8-oxodihydropurine derivatives of the present invention have the position number of the purine ring as shown in the following formula (I):

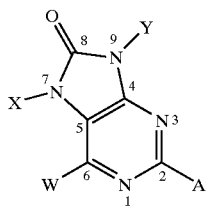

(I)

wherein A, W, X and Y are as defined above, and the nomenclature herein is based on said position number.

The following definitions apply to the terms as used throughout this specification.

The $C_{1-6}$ alkyl group and $C_{1-6}$ alkyl moiety may denote a straight chain or branched chain. Suitable examples of "$C_{1-6}$ alkyl group" are methyl, ethyl, propyl, isopropyl, butyl, isobutyl, pentyl, and hexyl, preferably those containing 1–4 carbon atoms. Suitable examples of "$C_{1-6}$ alkoxy group" are methoxy, ethoxy, propoxy, isopropoxy, and butoxy. The "$C_{3-6}$ alkenyl group" includes groups having 3–6 carbon atoms, containing one double bond at the position other than between 1 and 2 positions, such as allyl and 2-butenyl.

Suitable examples of "$C_{3-8}$ cycloalkyl group" are cyclopropyl, cyclobutyl, cyclopentyl, cyclohexyl, cycloheptyl, and cyclooctyl. The "$C_{3-8}$ cycloalkyl-$C_{1-4}$ alkyl group" denotes an alkyl group having 1–4 carbon atoms, which is substituted by above "$C_{3-8}$ cycloalkyl group", such as cyclopropylmethyl, cyclopentylmethyl, and cyclohexylmethyl. The "hydroxy-$C_{1-4}$ alkyl group" denotes a $C_{1-4}$ alkyl group substituted by a hydroxy group, such as hydroxymethyl, 2-hydroxyethyl, and 3-hydroxypropyl. The "halogen atom" denotes fluorine, bromine, chlorine, and iodine. The "mono- or di($C_{1-4}$ alkyl)amino group" denotes an amino group substituted by 1 or 2 of alkyl groups having 1–4 carbon atoms, such as methylamino, ethylamino, propylamino, dimethylamino, diethylamino, dipropylamino, and ethylmethylamino.

Suitable examples of "phenyl group which may optionally have 1 or 2 substituents selected from a halogen, a $C_{1-6}$ alkyl, a $C_{1-6}$ alkoxy, a trifluoromethyl, a hydroxy, an amino, a mono- or di($C_{1-4}$ alkyl)amino, a cyano and a nitro" are phenyl; 2-, 3- or 4-chlorpheny; 2-, 3- or 4-brompheny; 2-, 3- or 4-fluorophenyl; 2,4-dichlorophenyl; 2,4-dibromophenyl; 2,4-diflurophenyl; 2-, 3- or 4-methylphenyl; 2-, 3- or 4-methoxyphenyl; 2-, 3- or 4-trifluoromethylphenyl; 2-, 3- or 4-hydroxyphenyl; 2-, 3- or 4-aminophenyl; 2-, 3- or 4-methylaminophenyl; 2-, 3- or 4-dimethylaminophenyl; 2-, 3- or 4-cyanophenyl; and 2-, 3- or 4-nitrophenyl.

Suitable examples of "$C_{1-4}$ alkyl group substituted by a phenyl group which may optionally have 1 or 2 substituents selected from a halogen, a $C_{1-6}$ alkyl, a $C_{1-6}$ alkoxy, trifluoromethyl, hydroxy, amino, a mono- or di($C_{1-4}$ alkyl) amino, cyano and nitro" are benzyl; 2-, 3- or 4-chlorobenzyl; 2-, 3- or 4-bromobenzyl; 2-, 3- or 4-fluorobenzyl; 2,4-dichlorobenzyl; 2,4-dibromobenzyl; 2,4-difluorobenzyl; 2-, 3- or 4-methylbenzyl; 2-, 3- or 4-methoxybenzyl; 2-, 3- or 4-trifluoromethylbenzyl; 2-, 3- or 4-hydroxybenzyl; 2-, 3- or 4-aminobenzyl; 2-, 3- or 4-methylaminobenzyl; 2-, 3- or 4-dimethylaminobenzyl; 2-, 3- or 4-cyanobenzyl; 2-, 3- or 4-nitrobenzyl; phenethyl; and 2-(4-chlorophenyl)ethyl.

The examples of the following formula [B]:

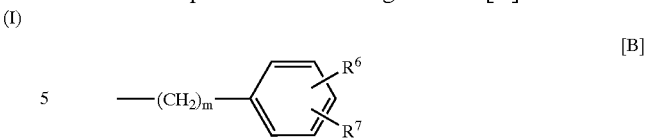

are just the above "phenyl group which may optionally have 1 or 2 substituents selected from a halogen, a $C_{1-6}$ alkyl, a $C_{1-6}$ alkoxy, a trifluoromethyl, a hydroxy, an amino, a mono- or di($C_{1-4}$ alkyl)amino, a cyano and a nitro" and the alkyl group having 1 and 2 carbon atoms which is substituted by the above "phenyl group which may optionally have 1 or 2 substituents selected from a halogen, a $C_{1-6}$ alkyl, a $C_{1-6}$ alkoxy, trifluoromethyl, hydroxy, amino, a mono- or di($C_{1-4}$ alkyl)amino, cyano and nitro", and are preferably phenyl; 4- or 3-chlorophenyl; 4- or 3-bromophenyl; 4- or 3-fluorophenyl; 4-methoxyphenyl; 4-trifluoromethylphenyl; 4-hydroxyphenyl; benzyl; 2-, 3- or 4-chlorobenzyl; 4-bromobenzyl; 3- or 4-fluorobenzyl; 4-methylbenzyl; 4-methoxybenzyl; 4-trifluoromethylbenzyl; 4-hydroxybenzyl; phenethyl; and 2-(4-chlorophenyl)ethyl.

Suitable examples of "monocyclic 5- or 6-membered heteroaryl group or bicyclic heteroaryl group composed of 5- or 6-membered heteroaryls which have at least one heteroatom selected from a nitrogen atom, an oxygen atom or a sulfur atom and is optionally substituted by a $C_{1-3}$ alkyl or trifluoromethyl" are 2-, 3- or 4-pyridyl; 5-methyl-2-pyridyl; 2- or 3-thienyl; 2- or 3-furyl; 2-, 4- or 5-pyrimidinyl; 2- or 3-pyrazinyl; 1-pyrazolyl; 2-imidazolyl; 2-thiazolyl; 3-isoxazolyl; 5-methyl-3-isoxazolyl; quinolyl; and isoquinolyl.

Preferred are compounds of the formula (I) wherein A is a group of the formula [A']:

(wherein $R^4$ is a hydrogen atom, a halogen atom, a $C_{1-6}$ alkyl group, a $C_{1-6}$ alkoxy group, a trifluoromethyl group, a hydroxy group, an amino group, a mono- or di($C_{1-4}$ alkyl) amino group, a cyano group or a nitro group; and $R^5$ is a hydrogen atom, a halogen atom, a $C_{1-6}$ alkyl group, a $C_{1-6}$ alkoxy group or a hydroxy group), a pyridyl group, a thienyl group or a furyl group; and W, X and Y are the same as defined above, or pharmaceutically acceptable acid addition salts thereof.

More preferred are compounds of the formula (I) wherein:
(a) X is a group of the following formula [Qx]:

—CH($R^{31}$)CON($R^{11}$)($R^{21}$)　　　　[Qx]

wherein $R^{11}$ is a $C_{1-6}$ alkyl group, and $R^{21}$ is a $C_{1-6}$ alkyl group or a group of the formula [B]:

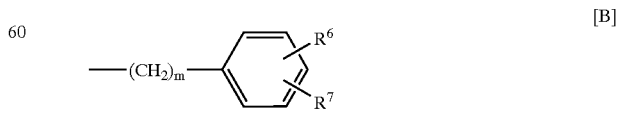

wherein $R^6$ is a hydrogen atom, a halogen atom, a $C_{1-6}$ alkyl group, a $C_{1-6}$ alkoxy group, a trifluoromethyl group, a hydroxy group, an amino group, a mono- or di($C_{1-4}$ alkyl)

amino group, a cyano group or a nitro group; $R^7$ is a hydrogen atom, a halogen atom, a $C_{1-6}$ alkyl group, a $C_{1-6}$ alkoxy group or a hydroxy group; and m is 0, 1, or 2, or $R^{11}$ and $R^{21}$ may optionally be taken together with the adjacent nitrogen to form a piperidine ring, a pyrrolidine ring, a morpholine ring or piperazine ring, which may optionally have 1 or 2 lower alkyl substituents respectively; $R^{31}$ is a hydrogen atom, a $C_{1-6}$ alkyl group, or a hydroxy-$C_{1-4}$ alkyl group, Y is a hydrogen atom or a $C_{1-6}$ alkyl group, (b) X is a hydrogen atom, a $C_{1-6}$ alkyl group, or a carbamoyl group; Y is a group of the formula [Qy]:

—CH($R^{31}$)CON($R^{11}$)($R^{21}$)  [Qy]

wherein $R^{11}$, $R^{21}$ and $R^{31}$ are as defined above;

A is a group of the above formula [A'], a pyridyl group, a thienyl group, or a furyl group;

W is as defined above, or pharmaceutically acceptable acid addition salts.

Further preferred are compounds of the formula (I) wherein:

(c) X is a group as defined in the above formula [Qx] (wherein $R^{11}$ is a methyl group; an ethyl group; a propyl group; an isopropyl group; or a butyl group;

$R^{21}$ is an ethyl group; a propyl group; an isopropyl group; a butyl group; a phenyl group; a phenyl group substituted by halogen, methoxy, trifluoromethyl or hydroxy; a benzyl group; a benzyl group substituted by halogen, methoxy, trifluoromethyl or hydroxy;

$R^{31}$ is as defined above);

Y is a hydrogen atom, a methyl group or an ethyl group, or (d) X is a hydrogen atom, a methyl group, an ethyl group, a propyl group, an isopropyl group or a butyl group;

Y is a group of the above formula [Qy] (wherein $R^{11}$ is a methyl group, an ethyl group, a propyl group, an isopropyl group or a butyl group;

$R^{21}$ is an ethyl group; a propyl group; an isopropyl group; a butyl group; a phenyl group; a phenyl group substituted by halogen, methoxy, trifluoromethyl or hydroxy; a benzyl group; a benzyl group substituted by halogen, methoxy, trifluoromethyl or hydroxy;

$R^{31}$ is as defined above;

A is a group of the above formula [A'], a pyridyl group, a thienyl group or a furyl group;

W is as defined above;

or pharmaceutically acceptable acid addition salts thereof.

Furthermore preferred are 2-aryl-8-oxodihydropurine derivatives of the formula (Ia):

(Ia)

wherein:

$R^{12}$ and $R^{22}$ are the same or different and are an ethyl group, a propyl group or a butyl group; or $R^{12}$ is a methyl group, an ethyl group or a propyl group, and $R^{22}$ is a phenyl group, a halogenophenyl group, a methoxyphenyl group, a benzyl group, a halogenobenzyl group or a methoxybenzyl group;

$R^{32}$ is a hydrogen atom, a methyl group or an ethyl group;

$Y^1$ is a hydrogen atom, a methyl group or an ethyl group;

$R^{42}$ is a hydrogen atom, a halogen atom, a methyl group, a methoxy group, a nitro group or a trifluoromethyl group; or the following formula (Ib):

(Ib)

wherein:

$X^1$ is a hydrogen atom, a methyl group, an ethyl group or a propyl group;

$R^{13}$ and $R^{23}$ are the same or different and are an ethyl group, a propyl group or a butyl group; or $R^{13}$ is a methyl group, an ethyl group or a propyl group, and $R^{23}$ is a phenyl group, a halogenophenyl group, a methoxyphenyl group, a benzyl group, a halogenobenzyl group or a methoxybenzyl group;

$R^{33}$ is a hydrogen atom, a methyl group or an ethyl group;

$R^{43}$ is a hydrogen atom, a halogen atom, a methyl group, a methoxy group, a nitro group or a trifluoromethyl group; or pharmaceutically acceptable acid addition salts thereof.

Preferred are the compounds of the formulas (Ia) and (Ib) wherein both $R^{32}$ and $R^{33}$ are each a hydrogen atom.

Specific examples of the compounds of the formulas (Ia) and (Ib) are as follows:

N-(4-methoxyphenyl)-7,8-dihydro-7-methyl-N-methyl-8-oxo-2-phenyl-9H-purine-9-acetamide (the test compound A as mentioned below);

N-benzyl-N-ethyl-8,9-dihydro-9-methyl-8-oxo-2-phenyl-7H-purine-7-acetamide (the test compound B as mentioned below); and N-benzyl-7-ethyl-N-ethyl-7,8-dihydro-8-oxo-2-phenyl-9H-purine-9-acetamide (the test compound D as mentioned below), or pharmaceutically acceptable acid addition salts thereof.

Especially preferable examples are the following compounds:

N-ethyl-8,9-dihydro-9-methyl-8-oxo-2-phenyl-N-phenyl-7H-purine-7-acetamide (the test compound C as mentioned below); and N-benzyl-N-ethyl-7,8-dihydro-7-methyl-8-oxo-2-phenyl-9H-purine-9-acetamide (the test compound E as mentioned below), and pharmaceutically acceptable acid addition salts thereof.

Suitable examples of the compounds of the formula (I) are the compounds of the examples in WO 99/28320 (the compounds in Examples 1–206).

The compounds of the formula (I) can be prepared by for example, the method described in WO 99/28320.

BEST MODE FOR CARRYING OUT THE INVENTION

The utility of the compounds of the present invention as a medicine for treatment and prevention of dementia will be illustrated by the test results thereof as to the typical compounds of the present invention, but is not limited thereto.

WO 99/28320 discloses the effects of the compounds of the formula (I) for the BZω$_3$ receptor, wherein it is shown that the compounds of the formula (I) have a selectivity and high-affinity to the BZ$\omega_3$ receptor.

The following compounds were used as the test compounds.

Test Compound A: N-(4-methoxyphenyl)-7,8-dihydro-7-methyl-N-methyl-8-oxo-2-phenyl-9H-purin-9-acetamide (the compound of Example 163 in WO 99/28320).

Test Compound B: N-benzyl-N-ethyl-8,9-dihydro-9-methyl-8-oxo-2-phenyl-7H-purin-7-acetamide (the compound of Example 54 in WO 99/28320).

Test Compound C: N-ethyl-8,9-dihydro-9-methyl-8-oxo-2-phenyl-N-phenyl-7H-purin-7-acetamide (the compound of Example 1 in WO 99/28320).

Test Compound D: N-benzyl-7-ethyl-N-ethyl-7,8-dihydro-8-oxo-2-phenyl-9H-purin-9-acetamide (the compound of Example 150 in WO 99/28320).

Test Compound E: N-benzyl-N-ethyl-7,8-dihydro-7-methyl-8-oxo-2-phenyl-9H-purin-9-acetamide (the compound of Example 146 in WO 99/28320).

Scopolamine is described in, for example, Merck Index, 12th Edition, 8550 (1996), and is commercially available, (for example, Sigma Aldrich Japan).

MK-801 is described in, for example, Merck Index, 12th Edition, 3451 (1996), and is commercially available, (for example, Sigma Aldrich Japan).

FGIN-1-27 can be prepared by the method described in JP-A-6-501030 (=WO 93/00334).

Learning/memory impairments in animals are usually induced by systemic administration of MK-801 (a noncompetitive antagonist for NMDA receptor which is a subtype of glutamic acid receptor) and scopolamine (a competitive antagonist for acetylcholine receptor), or intracerebral injection of β-amyloid peptide [Stephanie, D. et al., Eur. J. Pharmacol., 319, 1–4 (1997)].

Experiment 1: Ameliorating Effect on Spatial Memory Disorder Induced by Scopolamine.

The spatial memory test using Y-maze apparatus is a test to utilize the behavioral property of animals to enter into a new arm, avoiding the arm that they entered into just before (alternation behavior). This method is often used in order to study spatial working memory.

This experiment was carried out according to the method of Itoh, J., et al. [Eur. J. Pharmacol., 236, 341–345 (1993)].

Std-ddY male mice weighing 25–30 g (8 mice per one group) were used in the experiment. A solution of scopolamine in physiological saline (concentration: 0.06 mg/ml) was subcutaneously administered to mice in a volume of 0.1 ml/10 g of body weight, i.e., 0.6 mg/kg. Mice in the test compound group were orally treated with the test compound suspended in 0.5% tragacanth solution in a volume of 0.1 ml/10 g of body weight 1 hour before scopolamine administration, while animals in the amnesia control group and the vehicle control group received a 0.5% tragacanth solution in the same manner as above. However, the vehicle control group was injected with physiological saline instead of scopolamine. Thirty minutes after administration of scopolamine, the mice were placed at the end of the arm A of the Y-maze apparatus which was composed of three black acrylic trapezoid arms (bottom width: 3 cm, height of side wall: 12 cm, width of opened ceiling: 10 cm, length: 40 cm), wherein said three arms were connected at the one end of each arm to form Y-shape and another ends were closed, and the three arms were differentiated by the names as A, B and C respectively, and allowed to search freely the maze for 8 minutes. When the mouse was checked to enter into an arm at the length of not less than 10 cm from the entrance of the arm, the name of the arm (A, B or C) was recorded. It could be defined as a correct choice when the mouse selected the different three arms sequentially, and the number of alternation behavior i.e., the number of correct choices was counted. In the case that the total number of arm entries was less than 10 [the maximum number of alternation behavior (the number obtained by subtracting 2 from the total number of arm entries) is less than 8], the resulting data were not used and the retest was carried out instead, because the ability of learning could not occasionally reflect the alternation behavior. For the final data gotten, the ratio of the number of the alternation behavior to that of the entries (obtained by subtracting 2 from the total number of arm entries) was estimated as the rate of alternation behavior.

In statistical analysis, the rate of alternation behavior in the amnesia control group was compared with that in the vehicle control group by the nonparametric Wilcoxon rank sum test and it was checked if a significant amnesia was induced in the amnesia control group. Next, the efficacy of the test compounds was evaluated in comparison between the amnesia control group and the test compound group by the nonparametric Dunnett multiple comparison test. The statistical calculation was carried out with SAS system Version 6.12 (SAS Institute Japan Ltd.). Table 1 shows the minimum effective dose (MED), at which the significant ameliorating effect of the test compound on scopolamine-induced spatial memory disorder was observed at 5% significance level in the rate of alternation behavior.

The rate of alternation behavior in the amnesia control group with scopolamine significantly decreased to 40–47% while 61–70% in the vehicle control group, and hence, it was confirmed that the hypofunction of cholinergic system caused spatial memory disorder.

TABLE 1

| Test compounds | MED (mg/kg) |
|---|---|
| A | 3 |
| B | 3 |
| C | 0.01 |
| D | 3 |
| E | 1 |
| FGIN-1-27 | 10 |

The test compounds A–E exhibited a more potent ameliorating effect (MED <=3 mg/kg) than FGIN-1-27 did, especially the test compound C did further more (MED=0.01 mg/kg).

Experiment 2: Ameliorating Effect on Object Memory Disorder Induced by Scopolamine.

The object recognition test is a test method using the property which animals like to search a novel object. This method is often used in order to study the memorization and retention of episodic memory.

This experiment was carried out according to the partially modified method of Bartolini, L. et al. [Pharmacol. Biochem. Behav., 53, 277–283 (1996)].

Std-ddY male mice weighing 25–30 g (six mice per one group) were used in the experiment. Scopolamine dissolved in physiological saline (concentration: 0.04 mg/ml) was subcutaneously administered to mice in a volume of 0.1 ml per 10 g of body weight, i.e., 0.4 mg/kg. For the test compound group, the test compound suspended in 0.5% tragacanth solution was orally administered in a volume of 0.1 ml per 10 g of body weight, 30 minutes before scopolamine administration, and for the amnesia control group and the vehicle control group, a 0.5% tragacanth solution was administered in the same manner as above. However, for the vehicle control group, physiological saline was administered instead of scopolamine. Thirty minutes after the administration of scopolamine, the first trial was carried out for 5 minutes, and 1 hour after the first trial, the second trial was carried out for 5 minutes. In the first trial, the two same-shaped objects [red frustum-formed funnel adaptors made of silicon (bottom diameter: 6.1 cm, ceiling diameter: 4.5 cm, height: 3.5 cm)] are put on the two adjacent corners of the test box made of brown acrylic (length: 22.5 cm, width: 24.5 cm, height: 11 cm), and the time that the mouse explored each object was measured. In the second trial, the object (familiar: F) which the exploration time was longer in the first trial was retained, while another object in the first trial was replaced by the novel object [novel: N, red diver ring (outside diameter: 7.5 cm, inside diameter: 2.5 cm, thickness: 2.0 cm)] at the same position, and then the time for exploring each object was measured. The rate of object memory impairment was obtained from the formula: (N−F)/(N+F) as a discrimination index, and the comparison between the vehicle control group and the amnesia control group, and between the amnesia control group and the test compound group was carried out on the basis of said discrimination index.

In statistical analysis, the comparison between the vehicle control group and the amnesia control group was carried out by the Student's t test and it was checked whether a significant amnesia was induced. The efficacy of the test compounds was evaluated on the basis of comparison between the amnesia control group and the test compound group by the parametric Dunnett's multiple comparison test. The statistical calculation was carried out with SAS system Version 6.12 (SAS Institute Japan Ltd.). Table 2 shows the minimum effective dose (MED), which the significant difference in the discrimination index, as an ameliorating effect of the test compound on scopolamine-induced object memory impairment, was observed at 5% significance level.

The discrimination index in the scopolamine-induced amnesia group significantly decreased to 0.00–0.07 while it was 0.49–0.71 in the vehicle control group, and hence, it was confirmed that the hypofunction of cholinergic system caused object memory impairment.

TABLE 2

| Test compounds | MED (mg/kg) |
|---|---|
| C | 0.01 |
| E | 0.1 |
| FGIN-1-27 | >30 |

The test compound E exhibited a significant ameliorating effect at the dose of 0.1 mg/kg and the test compound C exhibited a significant ameliorating effect at low dose of 0.01 mg/kg. However, FGIN-1-27 exhibited no significant ameliorating effect at the dose of 30 mg/kg.

Experiment 3: Ameliorating Effect on the Impairment of Object Location Memory Induced by MK-801.

The object location memory test is a test method using the property which animals like to search a novelty caused by the change of an object location. This method is often used in order to study the ability of object location memory. This method is closely related with hypofunction of glutamatergic system and cause the location memory impairment selectively without the impairment of object memory which is induced by hypofunction of cholinergic system.

This experiment was carried out according to the partially modified method of Sophie L. Dix, et al. [Behav. Brain Res., 99, 191–200 (1999)].

Std-ddY male mice weighing 25–30 g (six mice per one group) were used in the experiment. A solution of MK-801 in physiological saline (concentration: 0.005 mg/ml) was subcutaneously administered in a volume of 0.1 ml per 10 g of body weight, i.e., 0.05 mg/kg. For the test compound group, the test compound suspended in 0.5% tragacanth solution was orally administered in a volume of 0.1 ml per 10 g of body weight, 30 minutes before MK-801 administration, and for the amnesia control group and the vehicle control group, a 0.5% tragacanth solution was administered in the same manner as above. However, for the vehicle control group, physiological saline was administered instead of MK-801. Thirty minutes after the administration of MK-801, the first trial was carried out for 5 minutes, and 1 hour after the first trial, the second trial was carried out for 5 minutes. In the first trial, the two same-shaped objects [red frustum-formed funnel adaptors made of silicon (bottom diameter: 6.1 cm, ceiling diameter: 4.5 cm, height: 3.5 cm)] were respectively put in the center and one of the corners of the test box made of brown acrylic (length: 22.5 cm, width 24.5 cm, height: 11 cm), and the time which the mouse explored each object was measured. In the second trial, the object (displaced object: DO) which was located in the center in the first trial was displaced in the opposite corner to another object (non displaced object: NDO), and then the time which the mouse explored each object was measured. The difference in the exploration time of DO and NDO respectively between the first trial and the second trial was calculated, and the comparison between the vehicle control group and the amnesia control group, and between the amnesia control group and the test compound group was carried out.

In statistical analysis, the comparison between the vehicle control group and the amnesia control group was carried out by the Student's t test and it was confirmed whether a significant object location memory impairment was induced. The efficacy of the test compounds was evaluated by comparing the amnesia control group with the test compound group using the parametric Dunnett's multiple comparison test. The statistical calculation was carried out with SAS system Version 6.12 (SAS Institute Japan Ltd.). Table 3 shows the minimum effective dose (MED), which a significant ameliorating effect on MK-801-induced object location memory impairment was observed at 5% significance level.

Besides, in the vehicle control group, the exploration time for NDO in the second trial decreased and the exploration time for DO was obviously longer than that for NDO. This result indicates that the change of the object location has a novelty and animals explored the object with novelty frequently. On the other hand, in the amnesia control group with MK-801, both exploration time for NDO and DO decreased remarkably. From these results, it was confirmed that MK-801 did not impair the memory of object itself, but impaired the memory of the object location.

TABLE 3

| Test compounds | MED (mg/kg) |
|---|---|
| C | 0.1 |
| E | 0.01 |
| FGIN-1-27 | 10 |

The test compound C exhibited a significant ameliorating effect at the dose of 0.1 mg/kg and the test compound E exhibited a significant ameliorating effect at low dose of 0.01 mg/kg, furthermore they were effective at less than 1/100 of the dose of FGIN-1-27.

Experiment 4: Acute Toxicity

The experiment on the test compound C was carried out using Std-ddY male mice weighing 25–30 g (10 mice per each group). The test compound suspended in 0.5% tragacanth solution was orally administered at the dose of 2000 mg/kg, and lethality of mice was observed for 7 days after the administration. As a result, no mouse treated with the test compound C died.

Experiment 5: Acute Toxicity 2

The experiment on the test compound E was carried out using Std-ddY male mice weighing 22.9–25.6 g (5 mice per each group) and Std-Wistar male rats weighing 126.6–136.6 g (5 rats per each group). The test compound suspended in 0.5% tragacanth solution was orally and intraperitoneally administered to the mice at the dose of 2000 mg/kg, and lethality of mice was observed for 7 days after the administration. As a result, no mouse treated with the test compound E died.

As is apparent from the above results, the compounds of the formula (I) exhibit an extremely potent ameliorating effects on learning and/or memory impairments induced by the systemic administration of MK-801 (noncompetitive antagonist for NMDA receptors, a subtype of glutamate receptors) and scopolamine (competitive antagonist for acetylcholine receptors) even at a low dose and further have a low toxicity, and hence, the compounds will be useful as a medicine for treatment and prevention of learning and/or memory impairments in mammals (including human beings), and also for treatment and prevention of dementia. In more detail, the compounds of the formula (I) may be useful as a medicine for treatment and prevention of learning deficit, dysmnesia, disorientation based on dysmnesia, and intellectual dysfunction, which are core symptoms of dementia. The intellectual dysfunction herein means not only dysmnesia but also the state of decline in calculational ability, abstract thinking ability, linguistic function and discretion so that the subject cannot keep a usual life and a social life.

Besides, the compounds of the formula (I) may be useful as a medicine for treatment and prevention of dementia such as Alzheimer-type dementia, cerebrovascular dementia and/or senile dementia, since said compounds exhibit a potent ameliorating effect on learning and/or memory impairments.

Further, the compounds of the formula (I) may be useful as a medicine for treatment and prevention of higher brain dysfunction in view of their potent ameliorating effect on learning and/or memory disorder. The higher brain dysfunction herein means brain dysfunctions involved in perception, attention, learning, memory, formation of concept, postulation, discretion, language, abstract thinking, action, recognition and behavior, etc., which are accompanied with dementia, aphasia, apraxia, agnosia, dyslexia, unilateral spatial neglect, dysmnesia, attention disorder, etc.

Moreover, the compounds of the formula (I) may be useful as a medicine for treatment and prevention of learning deficit, dysmnesia, disorientation based on dysmnesia and higher brain dysfunction associated therewith, in view of their potent ameliorating effect on learning disorder and/or dysmnesia. That is to say, the compounds of the formula (I) may be useful as a medicine for treatment and prevention of dementia symptoms associated with diseases which may cause dementia (for example, Alzheimer's disease, Pick' disease, Huntington's disease, Parkinson's disease, Down syndrome, schizophrenia, spinocerebellar degeneration, multiple cerebral infarction, intracerebral bleeding, Binswanger's disease, normal pressure hydrocephalus, chronic subdural hematoma, brain tumor, hypothyroidism, encephalitis, meningitis, disuse syndrome, Creutzfeldt-Jacob disease, head injury), since said compounds exhibit potent ameliorating effects on learning disorder and/or dysmnesia.

The compounds of the formula (I) may be administered through any of oral, parenteral and intrarectal routes. The dosage thereof may vary depending on the kinds of the compounds, administration routes, symptom/age of patients, etc., but it is usually in 0.01–50 mg/kg/day, preferably 0.03–5 mg/kg/day.

The compounds of the formula (I) are usually administrated in the form of a pharmaceutical preparation, which is prepared in admixture with conventional and pharmaceutically acceptable carrier or diluent. The pharmaceutically acceptable carrier may be any conventional ones which are commonly used in the pharmaceutical field and do not react with the compounds of the formula (I). Suitable examples are lactose, inositol, glucose, mannitol, dextran, cyclodextrin, sorbitol, starch, partially gelatinized starch, sucrose, magnesium aluminometasilicate, synthetic aluminum silicate, crystalline cellulose, sodium carboxymethylcellulose, hydroxypropyl starch, calcium carboxymethylcellulose, ion exchange resins, methylcellulose, gelatin, gum acacia, hydroxypropylcellulose, low-substituted hydroxypropylcellulose, hydroxypropylmethylcellulose, polyvinylpyrrolidone, polyvinyl alcohol, alginic acid, sodium alginate, light anhydrous silicic acid, magnesium stearate, talc, carboxyvinyl polymer, titanium oxide, sorbitan fatty acid ester, sodium lauryl sulfate, glycerin, glycerin fatty acid ester, purified lanolin, glycerogelatin, polysorbate, macrogol, vegetable oil, wax, propylene glycol, water, ethanol, polyoxyethylene hydrogenated castor oil (HCO), sodium chloride, sodium hydroxide, hydrochloric acid, sodium phosphate dibasic, sodium phosphate monobasic, citric acid, glutamic acid, benzyl alcohol, methyl p-oxybenzoate, ethyl p-oxybenzoate, etc.

Suitable examples of dosage forms are tablets, capsules, granules, powders, syrups, suspensions, suppositories, injection preparations, etc. These pharmaceutical preparations can be prepared by a conventional method. Liquid preparations may be in the form which is dissolved or suspended in water or other appropriate medium when used. Besides, tablets and granules may be coated in a conventional manner. Injection preparations may usually be prepared by dissolving the compound of the formula (I) in water, optionally using an isotonic agent or a solubilizer, and thereto may be also optionally added a pH adjusting agent, a buffering agent, and a preservative.

These preparations may usually contain the compound of the formula (I) in an amount of at least 0.01%, preferably 0.1–70%. These preparations may optionally contain other therapeutically effective ingredients.

The examples of the formulations of the medicine for the treatment and prevention of dementia according to the present invention are illustrated by the following preparations.

Preparation 1: Preparation of Tablets:

| | |
|---|---|
| N-benzyl-N-ethyl-7,8-dihydro-7-methyl-8-oxo-2-phenyl-9H-purin-9-acetamide | 1 g |
| Lactose | 84 g |
| Corn starch | 30 g |
| Crystalline cellulose | 25 g |
| Hydroxypropylcellulose | 3 g |

The above components are blended and granulated, and to the mixture are added light anhydrous silicic acid (0.7 g) and magnesium stearate (1.3 g), and then is compressed to prepare 1000 tablets (each tablet: 145 mg).

Preparation 2: Preparation of capsules:

| | |
|---|---|
| N-ethyl-8,9-dihydro-9-methyl-8-oxo-2-phenyl-N-phenyl-7H-purin-7-acetamide | 2 g |
| Lactose | 165 g |
| Corn starch | 25 g |
| Hydroxypropylcellulose | 3.5 g |
| light anhydrous silicic acid | 1.8 g |
| magnesium stearate | 2.7 g |

The above components are blended and granulated in a usual manner, and the resulting granules are filled in a capsule to prepare 1000 capsules (each 200 mg).

Preparation 3: Preparation of Powders:

| | |
|---|---|
| N-benzyl-N-ethyl-7,8-dihydro-7-methyl-8-oxo-2-phenyl-9H-purin-9-acetamide | 10 g |
| Lactose | 960 g |
| Hydroxypropylcellulose | 25 g |
| light anhydrous silicic acid | 5 g |

The above components are blended to prepare the desired powders in a usual manner.

INDUSTRIAL APPLICABILITY

As explained above, the compounds of the formula (I) exhibit extremely potent ameliorating effects on learning disorder and/or dysmnesia induced by hypofunction of glutamic acid neurons or acetylcholine neurons, and hence, they are expected to have potent ameliorating effect on intellectual dysfunction which is a core symptom of dementia such as Alzheimer-type dementia and cerebrovascular dementia, i.e., learning disorder and/or dysmnesia, disorientation due to dysmnesia, and higher brain dysfunction associated therewith, and they are useful for the treatment or prevention of dementia such as Alzheimer-type dementia, cerebrovascular dementia, and senile dementia.

What is claimed is:

1. A method for the treatment of Alzheimer-type dementia which comprises administering an effective amount of a 2-aryl-8-oxodihydropurine derivative of the formula (Ia):

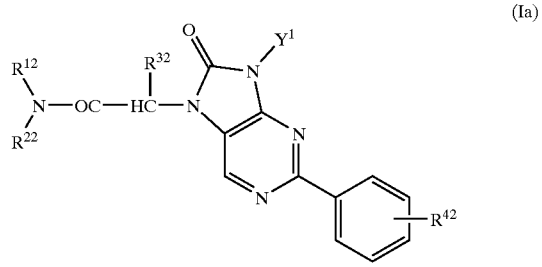

(Ia)

wherein:

$R^{12}$ and $R^{22}$ are the same or different and are an ethyl group, a propyl group or a butyl group; or $R^{12}$ is a methyl group, an ethyl group or a propyl group, and $R^{22}$ is a phenyl group, a halogenophenyl group, a methoxyphenyl group, a benzyl group, a halogenobenzyl group or a methoxybenzyl group;

$R^{32}$ is a hydrogen atom;

$Y^1$ is a hydrogen atom, a methyl group or an ethyl group;

$R^{42}$ is a hydrogen atom, a halogen atom, a methyl group, a methoxy group, a nitro group or a trifluoromethyl group, or a pharmaceutically acceptable acid addition salt thereof, to a mammal in need of such treatment of Alzheimer-type dementia.

2. A method for the treatment of Alzheimer-type dementia which comprises administering an effective amount of a 2-aryl-8-oxodihydropurine derivative of the formula (Ib):

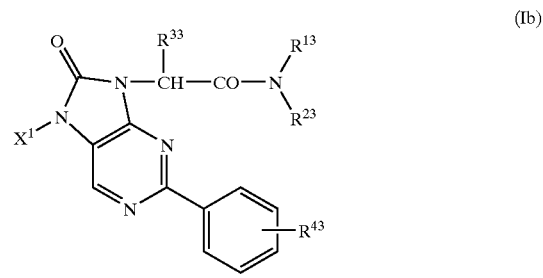

(Ib)

wherein:

$X^1$ is a hydrogen atom, a methyl group, an ethyl group or a propyl group;

$R^{13}$ and $R^{23}$ are the same or different and are an ethyl group, a propyl group or a butyl group; or $R^{13}$ is a methyl group, an ethyl group or a propyl group, and $R^{23}$ is a phenyl group, a halogenophenyl group, a methoxyphenyl group, a benzyl group, a halogenobenzyl group or a methoxybenzyl group;

$R^{33}$ is a hydrogen atom;

$R^{43}$ is a hydrogen atom, a halogen atom, a methyl group, a methoxy group, a nitro group or a trifluoromethyl group, or a pharmaceutically acceptable acid addition salt thereof, to a mammal in need of such treatment of Alzheimer-type dementia.

3. A method for the treatment of Alzheimer-type dementia which comprises administering an effective amount of a compound which is selected from the following compounds, N-(4-methoxyphenyl)-7,8-dihydro-7-methyl-N-methyl-8-oxo-2-phenyl-9H-purin-9-acetamide, N-benzyl-N-ethyl-8,9-dihydro-9-methyl-8-oxo-2-phenyl-7H-purin-7-acetamide, N-ethyl-8,9-dihydro-9-methyl-8-oxo-2-phenyl-N-phenyl-7H-purin-7-acetamide, and N-benzyl-7-ethyl-N-ethyl-7,8-dihydro-8-oxo-2-phenyl-9H-purin-9-acetamide, or a pharmaceutically acceptable acid addition salt thereof, to a mammal in need of such treatment of Alzheimer-type dementia.

4. A method for the treatment of Alzheimer-type dementia which comprises administering an effective amount of N-benzyl-N-ethyl-7,8-dihydro-7-methyl-8-oxo-2-phenyl-9H-purin-9-acetamide, or a pharmaceutically acceptable acid addition salt thereof, to a mammal in need of such treatment of Alzheimer-type dementia.

* * * * *